US011498887B2

(12) United States Patent
Delledonne et al.

(10) Patent No.: US 11,498,887 B2
(45) Date of Patent: Nov. 15, 2022

(54) PROCESS FOR PRODUCING DIENES

(71) Applicant: Versalis S.P.A., San Donato Milanese (IT)

(72) Inventors: Daniele Delledonne, Oleggio (IT); Alberto Cesana, Galliate (IT); Marco Mattachini, Mezzomerico (IT); Monica Vittoria Pastori, Cuggiono (IT)

(73) Assignee: Versalis S.P.A., San Donato Milanese (IT)

( * ) Notice: Subject to any disclaimer, the term of this patent is extended or adjusted under 35 U.S.C. 154(b) by 0 days.

(21) Appl. No.: 16/339,186

(22) PCT Filed: Oct. 18, 2017

(86) PCT No.: PCT/EP2017/076554
§ 371 (c)(1),
(2) Date: Apr. 3, 2019

(87) PCT Pub. No.: WO2018/073282
PCT Pub. Date: Apr. 26, 2018

(65) Prior Publication Data
US 2019/0241481 A1    Aug. 8, 2019

(30) Foreign Application Priority Data
Oct. 19, 2016   (IT) .................. 102016000105178

(51) Int. Cl.
| C01C 1/24 | (2006.01) |
| C07C 11/167 | (2006.01) |
| C07C 1/24 | (2006.01) |
| B01J 37/03 | (2006.01) |
| B01J 35/00 | (2006.01) |
| B01J 23/10 | (2006.01) |
| B01J 29/08 | (2006.01) |
| B01J 29/70 | (2006.01) |
| B01J 37/00 | (2006.01) |
| C07C 29/60 | (2006.01) |
| B01J 35/10 | (2006.01) |
| B01J 37/08 | (2006.01) |
| C07C 33/03 | (2006.01) |
| C12P 7/18 | (2006.01) |

(52) U.S. Cl.
CPC .............. *C07C 1/24* (2013.01); *B01J 23/10* (2013.01); *B01J 29/08* (2013.01); *B01J 29/084* (2013.01); *B01J 29/7007* (2013.01); *B01J 29/7034* (2013.01); *B01J 35/0006* (2013.01); *B01J 35/1057* (2013.01); *B01J 35/1066* (2013.01); *B01J 37/0018* (2013.01); *B01J 37/031* (2013.01); *C07C 29/60* (2013.01); *B01J 35/109* (2013.01); *B01J 37/08* (2013.01); *B01J 2229/37* (2013.01); *B01J 2229/42* (2013.01); *C07C 11/167* (2013.01); *C07C 33/03* (2013.01); *C07C 2529/08* (2013.01); *C07C 2529/70* (2013.01); *C12P 7/18* (2013.01)

(58) Field of Classification Search
CPC ................ B01J 35/0006; B01J 35/1057; B01J 35/1066; B01J 35/109; B01J 29/08; B01J 37/0018; B01J 37/031; B01J 37/08; B01J 23/10; B01J 29/084; B01J 29/7007; B01J 29/7034; B01J 2229/37; B01J 2229/42; C12P 7/18; C07C 1/24; C07C 29/60; C07C 11/167; C07C 33/03; C07C 2529/08; C07C 2529/70
See application file for complete search history.

(56) References Cited

U.S. PATENT DOCUMENTS

| 4,891,458 A * | 1/1990 | Innes ................... B01J 29/7007 585/323 |
| 2007/0087934 A1* | 4/2007 | R.M. Martens ......... B01J 29/80 502/64 |
| 2015/0225311 A1* | 8/2015 | Adam ..................... C08F 10/02 526/68 |
| 2016/0221904 A1* | 8/2016 | Sakami ..................... C07C 1/24 |
| 2016/0251281 A1 | 9/2016 | Song et al. |
| 2017/0349503 A1* | 12/2017 | Chinta .................. C07C 45/002 |

FOREIGN PATENT DOCUMENTS

| CN | 105712819 A | 6/2016 |
| JP | 2015182031 A | 10/2015 |

(Continued)

OTHER PUBLICATIONS

Nikitina et al. ("Dehydration of 2,3-butanediol over zeolite catalysts", Petroleum Chemistry vol. 56, 230-236, Published May 22, 2016). (Year: 2016).*

(Continued)

*Primary Examiner* — In Suk C Bullock
*Assistant Examiner* — Jason Y Chong
(74) *Attorney, Agent, or Firm* — Husch Blackwell LLP

(57) ABSTRACT

The present invention relates to a process for producing a diene, preferably a conjugated diene, more preferably 1,3-butadiene, comprising the dehydration of at least one alkenol having a number of carbon atoms greater than or equal to 4, in the presence of a catalytic material comprising at least one crystalline metalosilicate in acid form, preferably a macroporous zeolite, more preferably a zeolite with a FAU, BEA or MTW structure. Preferably, said alkenol having a number of carbon atoms greater than or equal to 4 may be obbtained directly through biosynthetic processes, or through catalytic dehydration processes of at least one diol. When said alkenol is a butenol, said diol is preferably a butanediol, more preferably 1,3-butanediol, even more preferably bio-1,3-butanediol, i.e. 1,3-butanediol deriving from biosynthetic processes. When said alkenol is 1,3-butanediol, or bio-1,3-butanediol, the diene obtained with the process according to the present invention is, respectively, 1,3-butadiene, or bio-1,3-butadiene.

18 Claims, No Drawings

(56) References Cited

FOREIGN PATENT DOCUMENTS

| JP | 2015182032 A | 10/2015 |
|---|---|---|
| TW | 201602068 A | 1/2016 |
| WO | 2015/146789 A1 | 10/2015 |
| WO | 2015/173780 A1 | 11/2015 |
| WO | 2016135609 A1 | 9/2016 |

OTHER PUBLICATIONS

International Search Report and Written Opinion for PCT/EP2017/076554 dated Jan. 4, 2018, 13 pages.
P. Reddy, J. Indian Chem. Soc., vol. 75, Oct.-Dec. 1998, pp. 688-689.
Veera Reddy, P. et al., "Novel Synthesis of Trioxatetracyclo [5.3.2.0.4,9.04,11] dodecane and Bibenzyl Skeletons" Tetrahedron Letters, vol. 39, 1629-1632, 1998.

\* cited by examiner

PROCESS FOR PRODUCING DIENES

The present invention relates to a process for producing dienes.

In particular, the present invention relates to a process for producing a diene, preferably a conjugated diene, more preferably 1,3-butadiene, comprising the dehydration of at least one alkenol having a number of carbon atoms greater than or equal to 4, in the presence of a catalytic material comprising at least one crystalline metalosilicate in acid form, preferably a macroporous zeolite, more preferably a zeolite with a FAU, BEA or MTW structure.

Preferably, said alkenol having a number of carbon atoms greater than or equal to 4 may be obtained directly through biosynthetic processes, or through catalytic dehydration processes of at least one diol.

When said alkenol is a butenol, said diol is preferably a butanediol, more preferably 1,3-butanediol, even more preferably bio-1,3-butanediol, i.e. 1,3-butanediol deriving from biosynthetic processes.

When said alkenol is 1,3-butanediol, or bio-1,3-butanediol, the diene obtained with the process according to the present invention is, respectively, 1,3-butadiene, or bio-1,3-butadiene, or 1,3-butadiene deriving from intermediates in turn deriving from biosynthetic processes.

1,3-butadiene is a fundamental product of the petrochemical industry, representing a substrate for the preparation, among other products, of chloroprene, adiponitrile, and hexamethylenediamine.

In fact, 1,3-butadiene is used in many industrial sectors, including plastic, synthetic rubber, resins, latexes, thermopolymers (e.g. ABS), paints and synthetic fibers. The copolymerization product of 1,3-butadiene with styrene enters into the composition of the mixtures for the production of tires.

More than 95% of the 1,3-butadiene produced annually is obtained as a subproduct deriving from steam cracking processes of hydrocarbons for producing ethylene and other olefins, from which it is separated through extractive distillation. 1,3-butadiene can also be obtained from fossil fuels through other processes, e.g. catalytic/oxidative dehydrogenation of butane and/or butenes. All these processes are particularly energy intensive and imply the emission of high quantities of $CO_2$.

The development of production processes for dienes, preferably conjugated, and in particular 1,3-butadiene, free from the production of ethylene, characterized by high productivity, reduced environmental impact and contained process costs, is therefore of great interest for industry. In particular, processes able to use materials deriving from biosynthetic processes and/or deriving from renewable sources have recently acquired increasingly greater importance.

The aforementioned biosynthetic processes are generally performed through micro-organisms able to use carbohydrates, e.g. sugars (glucose, xylose, arabinose, fructose and the like), of any origin, in particular from starches or from cellulose and hemicellulose present in biomasses.

The production of 1,3-butadiene from diols, in particular from 1,3-butanediol, is known in the art. For example, patent U.S. Pat. No. 2,310,809 describes a method for producing diolefins, in particular 1,3-butadiene, through catalytic dehydration of aliphatic glycols having at least four carbon atoms, which comprises placing said glycols in contact in the gaseous phase with a phosphorus based dehydration catalyst, in the presence of at least one organic compound brought into the vapor state (e.g. hexane, cyclohexane, tetrahydrofuran) and possibly water vapor. However, the aforementioned process is difficult to apply to industry since it envisages very low reagent feed rates (equal to 0.060 kg·h$^{-1}$·l$^{-1}$ of catalytic mixture) and in a particularly unfavorable dilution ratio with the vaporized organic compound and/or water, with the consequent low productivity of the catalyst. U.S. Pat. No. 2,237,866 also describes a process for preparing diolefins, in particular 1,3-butadiene, through catalytic dehydration in the vapor phase of glycols and the corresponding olefin alcohols, in the presence of a catalyst in the vapor state under the reaction conditions, containing phosphorus (e.g. volatile esters of phosphoric acid, phosphorus oxychloride, phosphorus trichloride, phosphrous pentachloride) co-fed with butanediol to overcome the problem of the deactivation of the catalyst but inducing a continuous and irreversible consumption of the catalyst itself to 2% by weight with respect to the fed butanediol.

Process U.S. Pat. No. 2,310,809 is characterized by the rapid deactivation of the catalyst: on that point, patent U.S. Pat. No. 2,426,678 describes a process having the aim of regenerating the dehydration catalysts based on phosphates, preferably ammonium phosphate, using volatile esters of phosphoric acid. However, this process only restores part of the catalytic activity and for a relatively limited time.

More recently, EP 2 952 498 A1 described a dehydration method for 2,3-butanediol to butadiene, characterized by the use of at least one catalyst selected from a mixed pyrophosphate of alkaline earth metals in which at least one of them is magnesium or strontium, a phosphate or a mixed pyrophosphate of lithium and an alkaline earth metal, in which the selectivity values for 1,3-butadiene obtained do not however exceed 59%. In the published application US2016/251281, a similar process is mentioned, wherein 2,3-butanediol is dehydrated in one step at high temperature, in the presence of a catalyst selected from acid phosphates, heteropolyacids, acid zeolites, silica-alumina. However, such a process is not specific to the achievement of 1,3-butadiene, in that it also produces relevant amounts of methylethylketone, that must be separated from the diene.

WO 2014/118484 A1 instead describes a process for obtaining dienes or polyenes through the dehydration of alcohols having three carbon atoms and different from propan-2-ol, in the presence of at least one or more metals selected from the group comprising the 14 lanthanides, yttrium, scandium and boron. In particular, the process is performed preferably in the gaseous phase, and envisages a marked dilution of the starting alcohol in nitrogen (in the examples, the alcohol/N$_2$ ratio varies between 1/49.5 and 1/82.6), which consequently makes it more difficult and uneconomic to recover the diene obtained.

Moreover, the use of different catalysts has not been shown to be satisfactory: for example C. R. Adams, in "Exploratory catalytic oxidations with bismuth molybdate" (1968), *J. Catalysis*, vol 10, pag. 355-361, described the oxidation of crotyl alcohol (2-buten-1-ol) and of its isomer methyl-vinyl-carbinol (3-buten-2-ol) providing 1,3-butadiene using catalysts based on bismuth molybdate in an oxidising environment. However, the same catalyst was shown to have an extremely limited selectivity for 1,3-butadiene (10-15%) when used in the dehydration of 1,3-butanediol to 1,3-butadiene through crotyl alcohol, as described, for example by C. R. Adams himself, in "Selectivity effects in some catalytic oxidation processes" (1969), *Ind. Eng. Chem.*, vol. 61, pag. 30-38.

The preparation of dienes starting from a diol having a number of carbon atoms greater than or equal to 4 can also be obtained through a two-stage process, which passes through the intermediate dehydration of said diol for obtaining a mixture of alkenols, in particular butenols, further subjected to dehydration obtaining the corresponding diene. For example, the preparation process of 1,3-butadiene starting from 1,3-butanediol may be mediated by two different catalysts, according to the following diagram:

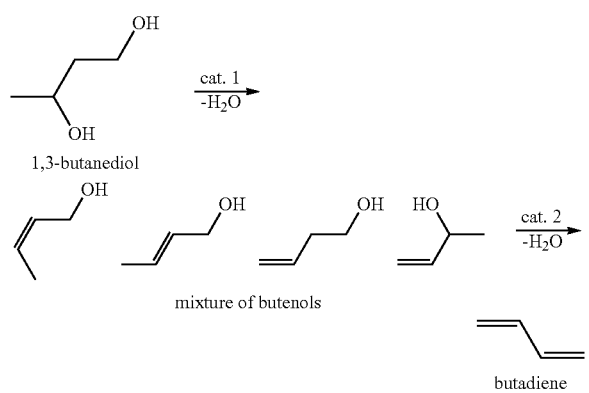

The first stage of the process can be performed with high conversion yields (>70%) and selectivity greater than 90 mol %, in temperature conditions <400° C. and using a cerium oxide based catalyst as described, for example, by S. Sato et al., in "Selective dehydration of diols to allylic alcohols catalyzed by ceria" (2003), *Catal. Commun.*, vol. 4, pag. 77-81 and by S. Sato et al., in "Dehydration of 1,3-butanediol over rare earth oxides" (2010) *Appl. Catal. A: General*, vol. 377, pag. 92-98.

The second stage of the aforementioned process comprises the dehydration of the alkenols to provide the corresponding dienes. The dehydration reaction of the methyl-vinyl-carbinol to 1,3-butadiene catalyzed by alumina, was already described by C. Prevost in 1928 in "Allylic transposition and addition compounds of erythrenic hydrocarbons. II. Experimental part (1): preparation, allylic transposition and dehydration of vinylcarbinols", *Ann. Chim.*, vol. 10, pag. 147-181.

The dehydration of crotyl alcohol to 1,3-butadiene in the presence of kaolin-H$_3$PO$_4$ or kaolin-Fe$_2$O$_3$-KOH as catalysts was instead described by H. Nagai in "Synthesis of butadiene by dehydration of crotyl alcohol" (1943), *J. of the Chemical Society of Japan*, vol. 46, pag. 1264-1265. In this case the yield of 1,3-butadiene with respect to alcohol is only 57%, even under the best conditions. Y. Gorin et al., in "Catalytic dehydration of unsaturated alcohols" (1962), *Kataliz Vysshei Shkole, Min. Vysshego Srednego Spets. Obrazov*, vol. 1958, pag. 258-267, investigated instead the catalytic dehydration reaction of unsaturated alcohols in the presence of different phosphate based catalysts, activated Al$_2$O$_3$, anhydrous MgSO$_4$, MgSO$_4$+SiO$_2$, Ta$_2$O$_5$+SiO$_2$. In this case the yields obtained are greater (88.5 mol %), but no information is provided on the durability and stability of the catalytic compositions used.

WO 2014/033129 describes the production of conjugated dienes starting from sources of carbon, in particular carbohydrates (e.g. glucose), polyols (e.g. glycerol), biodegradable polymers (e.g. amides, cellulose, poly-3-hydroxyalkenoates), which are converted microbiologically to alkenols which, in turn, are transformed enzymatically into the corresponding conjugated dienes.

However, it is important to note that, although enzymatic reactions show greater specificity than the corresponding chemical processes, they are typically characterized by lower yields due, for example, to retroactive enzyme inhibition phenomena, and higher costs.

Finally, the use is known of amorphous silica alumina as catalysts in the production of 1,3-butadiene from alkenols, as described, for example, by N. Ichikawa et al., in "Catalytic reaction of 1,3-butanediol over solid acids" (2006), *J. Mol. Catal. A*, vol. 256, pag. 106-112.

On this subject Italian patent application MI2015A000262, in the Applicant's name, describes a process for producing a diene, preferably a conjugated diene, more preferably 1,3-butadiene, comprising the dehydration of an alkenol in the presence of at least one catalytic material comprising at least one acid catalyst based on silica and alumina, preferably a silica alumina catalyst, in which the active phase of the aforementioned catalyst has an alumina content less than or equal to 12% by weight. In the dehydration reactions of alcohols catalyzed by acidic materials, besides the main product constituting the corresponding olefin, numerous other secondary products can be obtained, for example the ethers of the aforementioned alcohols, and further sub-products of secondary reactions, such as the cracking, dehydrogenation and/or oligomerization of the olefins obtained. These secondary products cause the catalytic material to get dirty, progressively reducing its activity until total deactivation. Although known, the phenomenon of the deactivation of the dehydration catalyst has not been studied in detail. One of the few studies on the deactivation mechanisms of alumina used as a dehydration catalyst of 2-methyl-3-buten-2-ol to isoprene is that by G. Greco et al., in "The coking of porous catalysts—Catalytic dehydration of 2-methyl-3-buten-2-ol over alumina" (1973), *J. Catal.*, vol. 30, pag. 155-167.

In general, the approach followed to limit the poisoning, dirtying, thermal degradation etc. of the catalytic material, passes through the optimization of the catalytic system and the process conditions as described, for example, by J. A. Moulijin et al., in "Catalyst deactivation: is it predictable? What to do?" (2001), *Appl. Catal. A: Gen.*, vol. 212, pag. 3-16.

It may also be just as advantageous to identify processes in which new catalysts are used characterized by high activity and selectivity, with higher resistance against the agents responsible for their deactivation and easy to regenerate.

The Applicant therefore set out to solve the problem of identifying a process for producing dienes, in particular conjugated dienes, more in particular 1,3-butadiene and even more in particular bio-1,3-butadiene with high yields, through the catalytic dehydration of at least one alkenol having a number of carbon atoms greater than or equal to 4, in particular of at least one alkenol deriving from biosynthetic processes, conventionally said bio-alkenol, in which the drawbacks of the prior art are overcome.

The Applicant has now identified a process for producing dienes that comprises the dehydration of at least one alkenol having a number of carbon atoms greater than or equal to 4, in the presence of a catalytic material comprising at least one macroporous zeolite, more preferably a zeolite having a FAU, BEA or MTW structure, which in fact allows the aforementioned drawbacks to be overcome.

Preferably, said linear or branched alkenol, has the general formula $C_nH_{2n}O$, n being an integer greater than or equal to 4 and less than or equal to 8, preferably greater than or equal to 4 and less than or equal to 6 and even more preferably equal to 4.

Preferably, the zeolite having a FAU structure may be a zeolite Y, described, for example, in U.S. Pat. No. 3,130,007, in any form comprising the different stabilized forms known to a person skilled in the art as described, for example, in U.S. Pat. No. 3,506,400, U.S. Pat, No. 3,929,672, or U.S. Pat. No. 5,242,677. Likewise, the FAU structure zeolite may be a zeolite Y treated so as to have a larger quantity of macropores as described, for example, in U.S. Pat. No. 5,601,798 and in WO 95/007236.

Preferably the zeolite having a BEA structure may be a zeolite Beta described, for example, in U.S. Pat. No. 3,308, 069.

Preferably the zeolite having an MTW structure may be a ZSM-12 zeolite described, for example, in U.S. Pat. No. 3,832,449.

The zeolite that can be used in the process according to the present invention may be in acid form or prevalently acid form, i.e. having most or all of the sites originally occupied by cations substituted by hydrogen ions. Said substitution may be performed with the methods known to a person skilled in the art, for example through ion exchange with ammonium salts and subsequent calcination.

Furthermore, said zeolite is characterised by a $SiO_2$/$Al_2O_3$ ratio (Silica:Alumina Ratio, SAR) which may be comprised between 7 and 60 and is preferably comprised between 10 and 30.

Said zeolite may be used in the process according to the invention as it is, or it may be subjected to forming, either in the presence or in the absence of a binder.

Numerous advantages are obtained thanks to the use of the aforementioned catalytic material in the process according to the invention.

For example, said catalytic material allows high conversion values of the starting alkenol and selectivity for the desired diene to be obtained. Furthermore, it displays constant catalytic activity over a prolonged interval of time, and can be easily regenerated and used again in the aforementioned process for producing dienes with excellent results. Furthermore, the use of the aforementioned catalytic material allows the process according to the present invention to be operated in a wide range of operating conditions, e.g. at different temperatures, at different contact times T, using different mixtures of alkenols, i.e. commercial mixtures of alkenols and/or deriving from biosynthetic processes and/or deriving from previous dehydration steps of diols. When the process in accordance with the invention is performed in the presence of a diluent of the alkenol, such as an inert gas, in particular $N_2$ or Ar, an organic solvent, in particular cyclohexane, tetrahydrofuran or benzene, or water, in particular the residual water deriving from the biosynthetic process used for producing the alkenol, as described better below, the alkenol:diluent molar ratio may be comprised in a wide range without this having negative consequences on the process itself.

As is known to a person skilled in the art, contact time T (expressed in seconds) means the ratio between the volume of catalytic material in a reactor (expressed in litres), and the volumetric feed rate of the reactor itself (expressed in liters/second) under the reaction conditions.

Further characteristics and advantages of the present invention will become clear from the following detailed description.

For the purposes of the present description and following claims, the definitions of the numeric ranges always include the extremes unless specified otherwise.

In the description of the embodiments of the present invention, the use of the terms "comprising" and "containing" indicates that the options described, for example regarding the steps of a method or of a process or the components of a product or of a device, are not necessarily all-inclusive. It is however important to note that the present application also relates to the embodiments in which the term "comprising" in relation to the options described, e.g. regarding the steps of a method or of a process or the components of a product or of a device, must be interpreted as "which essentially consists of" or "which consists of", even if this is not explicitly stated.

For the purpose of the present description and following claims, the percentages are always by weight, except in cases in which it is specified otherwise.

For the purposes of the present description and the following claims, "zeolite" generally means a hydrated aluminosilicate of alkaline metals and alkaline earth metals whose crystalline structure is based on a three-dimensional framework of tetrahedrals $TO_4$ (where T=Si or Al), joined together through the oxygen atoms, generating a set of interconnected empty spaces and channels, occupied by cations and by molecules of water, which confer peculiar controlled porosity characteristics to the zeolite. Further properties of a zeolite are reported by J. V. Smith in "Definition of a zeolite" (1984), *Zeolites*, vol. 4, pag. 309-310. As is known, due to its ability to promote interaction between the constituents of a reaction mixture, a zeolite may represent the active phase of numerous catalysts.

For the purposes of the present description and the following claims, "large pore zeolites", or "macroporous zeolites" means zeolites characterized by pores delimited by rings constituting 12 T atoms (where T=Si or Al), according to a classification known to a person skilled in the art reported, for example, in "Nanoscale Materials in Chemistry" (K. J Klabunde, R. Richards, Eds.) Second Edition 2009, John Wiley & Sons, Inc, pag. 334-335. Examples of macroporous zeolites are the zeolites of the FAU, BEA and MTW families.

Likewise, and with reference to the same classification, for the purposes of the present description and following claims, "medium pore zeolites", or "mesoporous zeolites" means zeolites characterized by pores delimited by rings constituting 10 T atoms (where T=Si or Al). An example of a mesoporous zeolite is ZSM-5, of the MFI zeolite family.

For the purposes of the present description and the following claims "specific surface area" means the total surface area of the particles of catalytic material contained in the unit of mass, measured with the method described by Brunauer, Emmett and Teller (BET method). The surface area can be determined by measuring the static absorption of nitrogen ($N_2$), at the temperature of liquid nitrogen (−196, 15° C.) with the ASAP ("*Accelerated Surface Area and Porosimetry System*") tool 2010 made by Micromeritics™, performed in accordance with the standard method ASTM D3663-03 (re-approved in 2015).

For the purposes of the present description and the following claims, every time reference is made to a compound, whether it is a reagent or a product, of which different stereoisomers may exist, for example isomers E-Z in the event in which there is at least a double bond between non-terminal $sp^2$ carbon atoms or enantiomers (R)—(S) in the event in which there is at least one asymmetrical $sp^3$ carbon, said reference to said compound comprises all its possible stereoisomers.

The subject matter of the present invention is a process for producing a diene, preferably a conjugated diene, more preferably 1,3-butadiene, comprising the dehydration of at least one alkenol having a number of carbon atoms greater than or equal to 4, in the presence of at least one catalytic material comprising at least one macroporous zeolite in acid or prevalently acid form, wherein said zeolite has a molar ratio $SiO_2/Al_2O_3$ (SAR) comprised between 7 and 60, preferably comprised between 10 and 30.

It is therefore clear that said zeolite constitutes the active phase of said catalytic material. The aforementioned catalytic material also comprises at least one inorganic binder, selected from the group consisting of silica, alumina, zirconium oxide, titanium oxide and mixtures thereof.

When the catalytic material comprises at least one inorganic binder, said inorganic binder may be present in quantities comprised between 5% and 90% by weight, preferably between 10% and 75% by weight, more preferably between 20% and 55% by weight, relative to the total weight of said catalytic material.

As is known to a person skilled in the art, to obtain a zeolite in acid, or prevalently acid, form, said zeolite, generally deriving from the synthesis in sodium or potassium form, can be subjected to ion exchange with an aqueous solution containing ammonium ions. The resulting zeolite in ammonic form, subjected to calcination, develops ammonia, produced by the thermal decomposition of the ammonium ions, conserving the $H^+$ ions within the crystal lattice, which give it the acid character. Zeolites are available on the market that already have acid characteristics, obtained as described above or with other processes. The acidity of a zeolite may be determined with any of the methods known to a person skilled in the art. For example, it can be measured by placing the catalytic material in contact with a base, for example pyridine, as described, for example, by C. A. Emeis, in "Determination of Integrated Molar Extinction Coefficients for Infrared Absorption Bands of Pyridine Adsorbed on Solid Acid Catalysts" (1993), *J. Catal.*, vol.141, pag. 347-354. The SAR ratio of a zeolite influences its chemical and physical characteristics, in particular the characteristics connected with the number and force of the acid sites. The SAR ratio can be determined through elementary analysis of the zeolite, for example through WD-XRF ("Wavelength Dispersion X-Ray Fluorescence"), with a PANanalytical Axios Advanced spectrometer equipped with a 4 kW X-ray tube with a rhodium anode. To obtain a zeolite having an SAR ratio comprised within a desired range, it may be sufficient, during the synthesis process of the zeolite itself, to use the source of Si and the source of Al in a molar ratio to one another equal to the desired SAR ratio. In fact, with sufficient approximation, the SAR ratio in the composition of the synthesis gel corresponds to the SAR ratio of the zeolite, except in cases in which the $SiO_2$ fraction is very large or very small. Therefore, for practical purposes, in most cases the SAR ratio of a zeolite contained in a catalytic material can be considered equivalent to the SAR ratio in the composition of synthesis gel of said zeolite.

Despite this, it is important to note that the SAR ratio can be changed post-synthesis, for example through controlled treatment with water vapor ("steaming"), as explained in U.S. Pat. No. 3,293,192 or U.S. Pat. No. 3,449,070, which removes part of the aluminum in the structure and hence makes the zeolite more thermally stable; the zeolite obtained, defined as stabilized or ultra stabilized ("Ultra Stabilized Y", USY), may be more catalytically active.

It is important to note that any treatment that aims to confer acid, or prevalently acid, behavior to said zeolite, such as an ion exchange process, can be performed without the SAR ratio of the zeolite being changed.

The SAR ratio can be determined, with the method indicated above, downstream of the treatment that significantly changed said ratio.

In any case, for the purposes of the present description and the following claims, the SAR ratio of said zeolite in said catalytic material always refers to the active phase i.e. to said macroporous zeolite in acid, or prevalently acid, form, regardless of any presence, in the catalytic material that comprises it, of inorganic binders and/or additional additives for the forming of said zeolite.

In other words, in the embodiment of the invention that envisages the use of a catalytic material comprising at least one inorganic binder, the process for producing a diene, preferably a conjugated diene, more preferably 1,3-butadiene, comprises the dehydration of at least one alkenol having a number of carbon atoms greater than or equal to 4, is performed in the presence of at least one catalytic material obtained through the forming of at least one macroporous zeolite in acid, or prevalently acid, form, having a molar ratio $SiO_2/Al_2O_3$ (SAR) comprised between 7 and 60, preferably comprised between 10 and 30, in the presence of said at least one inorganic binder.

To perform the process according to the present invention, the aforementioned catalytic material comprising at least one macroporous zeolite in acid, or prevalently acid, form, can be prepared with processes known in the art and can be used in various forms. In a preferred aspect, said macroporous zeolite in acid, or prevalently acid, form can be used as it is, or it may be formed, optionally in the presence of at least one inorganic binder selected from the group consisting of silica, alumina, zirconium oxide, titanium oxide and mixtures thereof.

To perform the forming operation, it is possible to operate according to one of the known methods as described, for example, by M. Campanati et al., in "Fundamentals in the preparation of heterogeneous catalysts" (2003), *Catal. Today*, vol. 77, pag. 299-314. The forming can be performed through extrusion, spherudizing, tableting, granulation, spray drying, or the like.

When the catalytic material obtained after the forming of said macroporous zeolite comprises at least one inorganic binder, said inorganic binder may be present in quantities comprised between 5% and 90% by weight, preferably between 10% and 75% by weight, more preferably between 20% and 55% by weight, relative to the total weight of said catalytic material.

In order to facilitate the forming operations, it is possible to add to said macroporous zeolite at least one peptizing agent preferably selected from aqueous solutions of: acetic acid, nitric acid, ammonium hydroxide. Said peptizing agent can be mixed with said macroporous zeolite and with the inorganic binder prior to forming, until a uniform paste is obtained.

To improve the rheological characteristics of the catalytic material, during the forming step it is possible to add one or more organic additives. These additives may preferably comprise: starches, cellulose or derivatives thereof, stearates, glycols, surfactants, or a mixture thereof.

At the end of the forming step, the catalytic material may be in different forms, for example such as spheres, microspheres, granules, pellets, extruded cylindrical, three-lobe, four-lobe forms, etc. and may possibly be subjected to calcination.

The aforementioned calcination can be performed in a muffle furnace, at a temperature comprised between 250° C. and 1200° C., preferably comprised between 450° C. and 800° C., for a time comprised between 1 hour and 36 hours, preferably comprised between 2 hours and 24 hours, even more preferably comprised between 4 hours and 18 hours. Said possible calcination can be performed in air, or in the presence of an inert gas (e.g. nitrogen), and is preferably performed in air.

In a preferred aspect of the invention, said macroporous zeolite is a zeolite having a FAU structure, or a BEA structure or an MTW structure.

More preferably, said macroporous zeolite is a zeolite having a FAU structure, or a BEA structure.

In an embodiment of the invention, said macroporous zeolite may be a zeolite having a FAU structure.

In a preferred aspect, said zeolite having a FAU structure may be a zeolite Y.

When the zeolite having a FAU structure is a zeolite Y, said zeolite Y may be characterized by a molar ratio $SiO_2/Al_2O_3$ (SAR) preferably comprised between 7 and 60, more preferably comprised between 10 and 30.

In a particularly preferred aspect of the invention, when said macroporous zeolite having a FAU structure is a zeolite Y, said zeolite Y is characterized by a molar ratio $SiO_2/Al_2O_3$ (SAR) comprised between 12 and 30.

Therefore, in a preferred embodiment of the present invention, the aforementioned process for producing a diene, preferably a conjugated diene, more preferably 1,3-butadiene, comprises the dehydration of at least one alkenol having a number of carbon atoms greater than or equal to 4, in the presence of at least one catalytic material comprising at least one zeolite Y in acid or prevalently acid form, wherein said zeolite Y has a molar ratio $SiO_2/Al_2O_3$ (SAR) comprised between 7 and 60, preferably comprised between 10 and 30, more preferably comprised between 12 and 30.

In a preferred aspect, said catalytic material comprises at least one inorganic binder, selected from the group consisting of silica, alumina, zirconium oxide, titanium oxide and mixtures thereof, preferably silica.

In a particularly preferred aspect said catalytic material comprises a zeolite Y in acid, or prevalently acid, form, in which said zeolite Y has a molar ratio $SiO_2/Al_2O_3$ (SAR) comprised between 12 and 30 and an inorganic binder containing silica.

For the purposes of the present invention, said zeolite Y may be used as it is or in stabilized or ultra stabilized form (USY), in acid or prevalently acid form, as described above.

Preferably, said linear or branched alkenol, has the general formula $C_nH_{2n}O$, n being an integer greater than or equal to 4 and less than or equal to 8, preferably greater than or equal to 4 and less than or equal to 6 and even more preferably equal to 4.

In an embodiment of the invention, said macroporous zeolite may be a zeolite having a BEA structure.

In a preferred aspect, said zeolite having a BEA structure is a zeolite Beta.

When the zeolite having a BEA structure is a zeolite Beta, said zeolite Beta may be characterized by a molar ratio $SiO_2/Al_2O_3$ (SAR) preferably comprised between 7 and 60, more preferably comprised between 10 and 30.

In a particularly preferred aspect of the invention, when said macroporous zeolite having a BEA structure is a zeolite Beta, said zeolite Beta is characterized by a molar ratio $SiO_2/Al_2O_3$ (SAR) comprised between 25 and 30.

Therefore, in a preferred embodiment of the present invention, the aforementioned process for producing a diene, preferably a conjugated diene, more preferably 1,3-butadiene, comprises the dehydration of at least one alkenol having a number of carbon atoms greater than or equal to 4, in the presence of at least one catalytic material comprising at least one zeolite Beta in acid or prevalently acid form, wherein said zeolite Beta has a molar ratio $SiO_2/Al_2O_3$ (SAR) comprised between 7 and 60, preferably comprised between 10 and 30, more preferably comprised between 25 and 30.

In a preferred aspect, said catalytic material comprises at least one inorganic binder, selected from the group consisting of silica, alumina, zirconium oxide, titanium oxide and mixtures thereof, preferably alumina.

In a particularly preferred aspect said catalytic material comprises a zeolite Beta in acid, or prevalently acid, form, in which said zeolite Beta has a molar ratio $SiO_2/Al_2O_3$ (SAR) comprised between 25 and 30 and an inorganic binder containing alumina.

In particular, pseudoboehmite can be used as a source of alumina.

Preferably, said linear or branched alkenol, has the general formula $C_nH_{2n}O$, n being an integer greater than or equal to 4 and less than or equal to 8, preferably greater than or equal to 4 and less than or equal to 6 and even more preferably equal to 4.

In the process for producing a diene, preferably a conjugated diene, more preferably 1,3-butadiene, according to the present invention, the catalytic material described above is used for the catalytic dehydration of at least one alkenol having a number of carbon atoms greater than or equal to 4.

Preferably, said linear or branched alkenol, has the general formula $C_nH_{2n}O$, n being an integer greater than or equal to 4 and less than or equal to 8, preferably greater than or equal to 4 and less than or equal to 6 and even more preferably equal to 4.

Specific examples of alkenols particularly useful for the purpose of the present invention are: 2-buten-1-ol, 3-buten-1-ol, 3-buten-2-ol, 2-methyl-3-buten-2-ol, 4-penten-1-ol, 4-penten-2-ol, 4-penten-3-ol, 3-penten-1-ol, 3-penten-2-ol, 2-penten-1-ol, 5-hexen-1-ol, 5-hexen-2-ol, 5-hexen-3-ol, 5-hexen-4-ol, 4-hexen-1-ol, 4-hexen-2-ol, 4-hexen-3-ol, 3-hexen-1-ol, 3-hexen-2-ol, 2-hexen-1-ol, 2-methyl-3-penten-2-ol, 2-methyl-4-penten-2-ol, 3-methyl-4-penten-2-ol, 6-hepten-1-ol, 6-hepten-2-ol, 6-hepten-3-ol, 6-hepten-4-ol, 6-hepten-5-ol, 5-hepten-1-ol, 5-hepten-2-ol, 5-hepten-3-ol, 5-hepten-4-ol, 4-hepten-1-ol, 4-hepten-2-ol, 4-hepten-3-ol, 3-hepten-1-ol, 3-hepten-2-ol, 2-hepten-1-ol, 7-octen-1-ol, 7-octen-2-ol, 7-octen-3-ol, 7-octen-4-ol, 7-octen-5-ol, 7-octen-6-ol, 6-octen-1-ol, 6-octen-2-ol, 6-octen-3-ol, 6-octen-4-ol, 6-octen-5-ol, 5-octen-1-ol, 5-octen-2-ol, 5-octen-3-ol, 5-octen-4-ol, 4-octen-1-ol, 4-octen-2-ol, 4-octen-3-ol, 3-octen-1-ol, 3-octen-2-ol, 2-octen-1-ol.

In a particularly preferred aspect of the invention, said alkenol has a number of carbon atoms equal to 4 and is therefore a butenol.

Preferably, said butenol is selected from the group consisting of 2-buten-1-ol (crotyl alcohol), 3-buten-2-ol (methyl-vinyl-carbinol), 3-buten-1-ol (allylcarbinol), and mixtures thereof and, even more preferably, said butenol is selected from the group consisting of 2-buten-1-ol, 3-buten-2-ol and mixtures thereof.

As already pointed out, when the alkenol can exist in different enantiomeric or stereoisomeric forms, it means that the process of the present invention can be performed with each of these, either in purified form or in a mixture.

For example, in the aforementioned process, the isomer E (trans) of 2-buten-1-ol, the isomer Z (cis) of 2-buten-1-ol or a mixture of said two isomers can be used indifferently. Likewise, in the aforementioned process, the enantiomer (R) of 3-buten-2-ol, the enantiomer (S) of 3-buten-2-ol, or a mixture of said two enantiomers can be used. In a preferred aspect of the invention, said alkenol having a number of carbon atoms greater than or equal to 4 may be obtained directly through biosynthetic processes, or through catalytic dehydration processes of a diol.

In a preferred aspect of the invention, when said alkenol has a number of carbon atoms equal to 4, and is therefore a butenol, said butenol is obtained through catalytic dehydration of a butanediol, preferably 1,3-butanediol, in the presence of a cerium oxide based catalyst, wherein said cerium oxide based catalyst is obtained through precipitation, in the presence of at least one base, of at least one compound containing cerium. Further details relative to said process can be found in international patent application WO 2015/173780 in the name of the Applicant and included herein as reference.

Preferably said diol, preferably a butanediol, more preferably 1,3-butanediol, can derive from the fermentation of sugars, preferably from the fermentation of sugars deriving from biomass.

For the purposes of the present description and the following claims, the term "biomass" indicates any organic material of plant origin that comprises: products deriving from agriculture, such as, plants and parts of the following plants: guayule, thistle, corn, soy, cotton, linen, rape, sugar cane, palm, including scraps, residues and waste deriving from said products or from their processing: products deriving from crops of plant species expressly cultivated for energy use, such as miscanthus, panic, giant cane, including scraps, residues and waste deriving from said products or their processing; products deriving from forestation or from forestry, including scraps, residues and waste deriving from said products or from their processing; scraps of agri-food products intended for human food or zootechnics; residues from the paper industry; waste from the separate collection of solid urban waste, such as scraps and residues of fruit and vegetables, paper.

In a particularly preferred aspect of the invention, said diol, preferably a butanediol, more preferably 1,3-butanediol, derives from the fermentation of sugars deriving from guayule biomass and/or from thistle, including scraps, residues, waste from guayule and/or thistle or from their processing.

Preferably said diol, preferably a butanediol, more preferably 1,3-butanediol, derives from the fermentation of sugars deriving from guayule biomass, including scraps, residues, waste from guayule and from its processing.

To produce the aforementioned sugars, said biomass is subjected to physical treatments (e.g. extrusion, steam explosion and the like), and/or to chemical hydrolysis and enzymatic hydrolysis, obtaining mixtures of carbohydrates, of aromatic compounds and of other products that derive from cellulose, hemicellulose and lignin present in biomass. In particular, the carbohydrates obtained are mixtures of glucides with 5 and 6 carbon atoms that include, for example, saccharose, glucose, xylose, arabinose, galactose, mannose and fructose, that will be used in fermentation. Processes relative to the production of sugars from biomass, in particular sugars from lignocellulosic biomass, are described in the art, for example, in international patent application WO 2015/087254, in the name of the Applicant.

Further biotechnological processes for obtaining bio-1,3-butanediol, starting from renewable sources, are described, for example, in U.S. Pat. No. 9,017,983 and in patent applications US 2012/0329113 and US 2013/0109064.

When the diol, preferably a butanediol, more preferably 1,3-butanediol, derives from biosynthetic processes, for example from the fermentation of sugars as described above, said diol is generally obtained in the form of an aqueous mixture. Before proceeding with the catalytic dehydration of the diol that leads to the obtaining of the corresponding alkenol, it is possible to subject the aforementioned aqueous mixture, comprising said diol obtained from biosynthetic processes, to common separation processes, such as total or partial distillation of the water and of the diol contained in said mixture. In fact, said aqueous mixture, after filtration and deionization, can be advantageously used as it is in the catalytic dehydration process that leads to the obtaining of the corresponding alkenol, without the need to subject it to expensive processes for removing the water or however limiting such removal.

In turn, the alkenol can be obtained in the form of an aqueous mixture.

Said aqueous mixture can be subjected to distillation, to recover the alkenol pure or in the form of an azeotrope with water, or used as it is.

For example, the catalytic dehydration of 1,3-butanediol leads to the obtaining of a mixture of butenols (2-buten-1-ol, 3-buten-2-ol, 3-buten-1-ol) that can be separated through distillation in the form of minimum azeotropes with water. The azeotropic mixtures of butenols may be used as they are, mixed together, or mixed together and have either butenols, in mixture or individually, or water added thereto, in order to be used in the catalytic dehydration process of the present invention for producing 1,3-butadiene.

In accordance with an embodiment of the present invention, in the aforementioned process for producing a diene, the at least one alkenol having a number of carbon atoms greater than or equal to 4, may be in a mixture with a diluent which can be selected, for example, from: an inert gas, for example nitrogen ($N_2$), argon (Ar), preferably $N_2$; or a compound having a boiling point comprised between 25° C. and 150° C. under normal conditions and preferably a boiling point comprised between 50° C. and 125° C. under normal conditions, and a melting point less than or equal to 20° C. under normal conditions. In a preferred aspect said compound is selected from the group consisting of water, tetrahydrofuran, cyclohexane, benzene, and mixtures thereof.

Nitrogen ($N_2$) and water are preferred, and water is particularly preferred.

It is important to note that said water may be residual water deriving from the biosynthetic process used for producing said at least one alkenol.

In a preferred aspect of the present invention, said process for producing a diene may be conducted, in the case in which the diluent is selected from inert gases, with a molar ratio between diluent and alkenol (or alkenols) greater than 0.3, preferably comprised between 0.5 and 2.

In a preferred aspect, when the diluent is selected from compounds having a boiling point comprised between 25° C. and 150° C. under normal conditions, preferably comprised between 50° C. and 125° C. under normal conditions and a melting point less than or equal to 20° C. under normal conditions, said process for producing a diene can be conducted with a molar ratio between diluent and alkenol (or alkenols) comprised between 0.01 and 100, preferably comprised between 0.1 e 50, more preferably comprised between 1 and 10.

The process according to the present invention can be conducted at a temperature comprised between 150° C. and 500° C., preferably comprised between 200° C. and 450° C., more preferably comprised between 250° C. and 400° C.

Said process can be conducted at a pressure of between 5 and 5000 kPa, preferably comprised between 30 and 350 kPa, more preferably comprised between 80 and 250 kPa.

The process according to the present invention can be conducted in the gas phase or the mixed liquid/gas phase.

In a preferred aspect of the invention, the aforementioned process is conducted in the gas phase.

Said process may be conducted in any type of reactor, preferably in a fixed bed reactor, a moving bed reactor or in a fluidized bed reactor.

In accordance with an embodiment of the present invention, said process can be conducted in a fixed bed reactor.

In the event that a fixed bed reactor is used, the catalytic material comprising at least one large pore zeolite can be split into various beds.

The reactor layout may comprise the recycling of part of the reaction effluents or of the catalytic material, in a "recirculated" reactor configuration.

In accordance with an alternative embodiment of the present invention, when the process according to the present invention is conducted in the mixed liquid/gas phase, a Continuous flow Stirred Tank Reactor (CSTR) can be used, containing the catalytic material in dispersion.

It is important to note that when in the process according to the present invention at least one alkenol is used, deriving from the catalytic dehydration of at least one diol, however the latter is obtained, the dehydration of said at least one diol to provide the at least one alkenol and the subsequent dehydration of said at least one alkenol to provide the diene can be performed:

in the same reactor or in different reactors, and preferably in different reactors;
continuously or discontinuously, and preferably continuously.

The process according to the present invention can also be performed continuously in a reactor configuration envisaging at least two reactors in parallel, preferably two fixed bed reactors in parallel, in which, when one reactor is operating, the catalytic material can be regenerated in the other reactor.

When the process is conducted continuously, the WHSV (Weight hourly space velocity), i.e. the ratio between the quantity by weight of reagent fed to the reactor and the quantity by weight of catalyst in the reactor itself, may be comprised between 0.5 h$^{-1}$ and 10 h$^{-1}$ and is preferably comprised between 1 h$^{-1}$ and 5 h$^{-1}$.

The contact time τ, calculated as a ratio of the volume of catalytic material loaded into the dehydration reactor to the volumetric feed rate under the reaction conditions, is preferably comprised between 0.01 seconds and 10 seconds, more preferably comprised between 0.05 seconds and 8 seconds, even more preferably comprised between 0.1 seconds and 4 seconds.

For the purpose of putting the present invention into practice and illustrating it more clearly, below are some non-limitative examples.

EXAMPLE 1

Preparation of a Large Pore Zeolite Y Formed in the Presence of SiO$_2$ as the Binder 250.5 g of commercial zeolite Y (CBV 712, Zeolyst International™), having an SAR=12 and surface area of 730 m$^2$/g, were mixed with 91.3 g of fumed SiO$_2$ (cat. S5130 Sigma-Aldrich®) and 34 g of 2-hydroxypropyl cellulose (Klucel™ LF, Ashland®) in a planetary stirrer Erweka mod. AR 402, for about 2 hours at the speed of 80 rpm.

After 2 hours, while still constantly stirring the material at 80 rpm, 290 g of demineralized water were added with a peristaltic pump over 4 hours (drop by drop) and finally 50 g of ethylene glycol over 1 hour (drop by drop).

The pasty mass obtained was transferred into a Bepex Hutt (Hosowaka-Bepex) extruder equipped with rollers with 2 mm holes, and extruded in pellets. After drying in the air for 24 hours the pellets were subjected to calcination at a temperature programmed according to the following gradient: from room temperature to 120° C. in 1 h; 120° C. constant for 2 h; from 120° C. to 350° C. in 3 h; 350° C. constant for 3 hour; from 350° C. to 550° C. in 3 hours; 550° C. constant for 6 hours. During the calcination, the zeolite loses NH$_3$ and is converted into a zeolite in acid form.

After cooling, the pellets were mechanically granulated and the fraction of granules having dimensions comprised between 0.5 mm and 1 mm was used as catalytic material. In the final catalytic material, the zeolite Y/SiO$_2$ ratio is 70/30.

EXAMPLE 2

Preparation of a Large Pore Zeolite Y Formed in the Presence of SiO$_2$ as the Binder 233 g of commercial zeolite Y in acid form (CBV 720, Zeolyst International™), having an SAR=30 and surface area of 780 m$^2$/g, were mixed with 90.1 g of fumed SiO$_2$ (cat. S5130 Sigma-Aldrich®) and 68.1 g of 2-hydroxypropyl cellulose (Klucel™ LF, Ashland®) in a planetary stirrer Erweka mod. AR 402, for about 2 hours at the speed of 80 rpm. After 2 hours, while still constantly stirring the material at 80 rpm, 355 g of demineralized water were added with a peristaltic pump over 4 hours (drop by drop) and finally 49 g of ethylene glycol over 1 hour (drop by drop).

The pasty mass obtained was transferred into a Bepex Hutt (Hosowaka-Bepex) extruder equipped with rollers with 2 mm holes, and extruded in pellets. After drying in the air for 24 hours the pellets were subjected to calcination at a temperature programmed according to the following gradient: from room temperature to 120° C. in 1 h; 120° C. constant for 2 h; from 120° C. to 350° C. in 3 h; 350° C. constant for 3 hour; from 350° C. to 550° C. in 3 hours; 550° C. constant for 6 hours.

After cooling, the pellets were mechanically granulated and the fraction of granules having dimensions comprised between 0.5 mm and 1 mm was used as catalytic material. In the final catalytic material, the zeolite HY/SiO$_2$ ratio is 70/30.

EXAMPLE 3

Preparation of a Macroporous Zeolite Y Formed in the Presence of Al$_2$O$_3$ as the Binder A catalyst based on ultra-high stabilized macroporous zeolite Y formed in the presence of alumina in the form of boehmite as the binder was prepared exactly as described in Example 1 of patent application WO 2004/056475, in the name of the Applicant.

In particular, 260 g of commercial zeolite Y (CBV 712 Zeolyst International™), having an SAR equal to 12 and a surface area of 730 m$^2$/g, were mixed with 278 g of pseudo-boehmite Versal V-250 and stirring was continued for 60 minutes before adding 310 ml of an aqueous solution of acetic acid at 0.5% by weight over about 30 minutes. After further stirring for about 15 minutes, the pasty mass obtained was extruded in the form of cylinders. After drying in a ventilated oven at 25° C. for 48 hours the pellets were subjected to calcination at a temperature programmed according to the following gradient: from room temperature to 120° C. in 3 h; 120° C. constant for 2 h; from 120° C. to 350° C. in 3 h; 350° C. constant for 4 hour; from 350° C. to 550° C. in 4 hours; 550° C. constant for 8 hours. During calcination, due to the loss of $NH_3$ the zeolite was converted into acid form.

The catalytic material obtained is in the form of rectangular cylinders with a diameter of about 2 mm and a length of about 7 mm.

In the final catalytic material, the zeolite Y/$Al_2O_3$ ratio is 50/50.

EXAMPLE 4

Preparation of a Macroporous Zeolite Beta Formed in the Presence of $Al_2O_3$ as the Binder A catalyst based on macroporous zeolite Beta formed in the presence of alumina in the form of boehmite as the binder was prepared exactly as described in Example 4 of EP 0847 802, in the name of the Applicant. In particular, after ion exchange treatment for obtaining the acid form, the macroporous zeolite Beta was mixed with the 50% by weight of $Al_2O_3$ (boehmite) as the binder, in the presence of acetic acid (0.028% by weight relative to the weight of the binder) as a peptizing agent. After 45 minutes of stirring, the pasty mass obtained was extruded into pellets. After drying, the catalytic material was subjected to a calcination treatment in air at 550° C. After cooling, the pellets were mechanically granulated and the fraction of granules having dimensions comprised between 0.5 mm and 1 mm was used as catalytic material.

The active form of said catalyst has an SAR equal to 28.

In the final catalytic material, the zeolite Beta/$Al_2O_3$ ratio is 50/50.

EXAMPLE 5

Preparation of a Macroporous Zeolite Beta Formed in the Presence of $SiO_2$ as the Binder 200 g of a 34% suspension by weight of colloidal silica (Ludox® TMA, Sigma-Aldrich cat. 420859) were placed in a 1 L beaker, and stirring was maintained at 220 rpm using a shaft stirrer.

71 g of commercial zeolite Beta (CP 814 E*, Zeolyst International™), having SAR=25 and surface area of 680 $m^2$/g were added to the above.

To facilitate the dispersion of the active phase in the dispersion of colloidal silica, during the addition the mechanical stirring speed was increased to 500 rpm. At the end, the stirring was set again to 220 rpm.

The mixture in suspension obtained was heated to 150° C. and kept at this temperature for 6 hours. The stirring was then gradually reduced in relation to the increase in viscosity of the mixture in suspension with the passing of time, until complete standstill, upon reaching the semi-solid state.

At the end, the material obtained was placed in an oven at 150° C. for 12 hours. The dried solid was transferred into a porcelain capsule and calcinated at 600° C. for 6 hours. After cooling, the solid material was mechanically granulated and the fraction of granules having dimensions comprised between 0.5 mm and 1 mm was used as catalytic material. In the final catalytic material, the zeolite Beta/$SiO_2$ ratio is 50/50.

COMPARATIVE EXAMPLE 6

Preparation of a Large Pore Zeolite Y with SAR=5.2, Formed in the Presence of $SiO_2$ as the Binder 249.5 g of commercial zeolite Y (CBV 500, Zeolyst International™), having an SAR=5.2 and surface area of 750 $m^2$/g, were mixed with 90 g of fumed $SiO_2$ (cat. S5130 Sigma-Aldrich®) and 34 g of 2-hydroxypropyl cellulose (Klucel™ LF, Ashland®) in a planetary stirrer Erweka mod. AR 402, for about 2 hours at the speed of 80 rpm.

After 2 hours, while still constantly stirring the material at 80 rpm, 301 g of demineralized water were added with a peristaltic pump over 4 hours (drop by drop) and finally 46 g of ethylene glycol over 1 hour (drop by drop).

The pasty mass obtained was transferred into a Bepex Hutt (Hosowaka-Bepex) extruder equipped with rollers with 2 mm holes, and extruded in pellets. After drying in the air for 24 hours the pellets were subjected to calcination at a temperature programmed according to the following gradient: from room temperature to 120° C. in 1 h; 120° C. constant for 2 h; from 120° C. to 350° C. in 3 h; 350° C. constant for 3 hour; from 350° C. to 550° C. in 3 hours; 550° C. constant for 6 hours. During calcination, the zeolite was converted into acid form.

After cooling, the pellets were mechanically granulated and the fraction of granules having dimensions comprised between 0.5 mm and 1 mm was used as catalytic material. In the final catalytic material, the zeolite Y/$SiO_2$ ratio is 70/30.

COMPARATIVE EXAMPLE 7

Preparation of a Mesoporous Zeolite ZSM-5 Formed in the Presence of $SiO_2$ as the Binder 200 g of a 34% suspension by weight of colloidal silica (Ludox® TMA, Sigma-Aldrich cat. 420859) were placed in a 1 L beaker, and stirring was maintained at 220 rpm using a planetary stirrer.

70 g of commercial zeolite ZSM-5 (CBV 2314, Zeolyst International™), having SAR=23 and surface area of 425 $m^2$/g were added to the above.

The mixture in suspension obtained was heated to 150° C. and kept at this temperature for 6 hours. The stirring was then gradually reduced in relation to the increase in viscosity of the mixture in suspension with the passing of time, until complete standstill, upon reaching the semi-solid state.

At the end, the material obtained was placed in an oven at 150° C. for 12 hours. The dried solid was transferred into a porcelain capsule and calcinated at 600° C. for 6 hours. After cooling, the solid material was mechanically granulated and the fraction of granules having dimensions comprised between 0.5 mm and 1 mm was used as catalytic material. In the final catalytic material, the zeolite ZSM-5/$SiO_2$ ratio is 50/50.

COMPARATIVE EXAMPLE 8

Preparation of a Mesoporous Zeolite ZSM-5 Formed in the Presence of $SiO_2$ as the Binder 201.8 g of a 34% suspension by weight of colloidal silica (Ludox® TMA, Sigma-Aldrich cat. 420859) were placed in a 1 L beaker, and stirring was maintained at 220 rpm using a planetary stirrer.

71 g of commercial zeolite ZSM-5 (CBV 8014, Zeolyst International™), having SAR=80 and surface area of 425 m$^2$/g were added to the above.

The mixture in suspension obtained was heated to 150° C. and kept at this temperature for 6 hours. The stirring was then gradually reduced in relation to the increase in viscosity of the mixture in suspension with the passing of time, until complete standstill, upon reaching the semi-solid state.

At the end, the material obtained was placed in an oven at 150° C. for 12 hours. The dried solid was transferred into a porcelain capsule and calcinated at 600° C. for 6 hours. After cooling, the solid material was mechanically granulated and the fraction of granules having dimensions comprised between 0.5 mm and 1 mm was used as catalytic material. In the final catalytic material, the zeolite ZSM-5/SiO$_2$ ratio is 50/50.

EXAMPLE 9

Preparation of the Mixture of Butenols through Catalytic Dehydration of 1,3-Butanediol To test the catalytic materials prepared as described in the Examples 1-8 above, tests were provided for the catalytic dehydration of a mixture of butenols, obtained by catalytic dehydration of 1,3-butanediol operating as described below.

Preparation of the Cerium Based Catalyst

The catalytic dehydration of 1,3 butanediol was performed using cerium oxide catalysts, as described in international patent application WO 2015/173780 in the name of the Applicant.

100 g of cerium nitrate hexahydrate (99% pure, Sigma-Aldrich®) were dissolved in a 2 L beaker in 1 kg of water, with a magnetic stirrer at 500 rpm, at room temperature (about 25° C.). The solution obtained was added over 2 hours, through a dropping funnel, in 1 kg of a 15% aqueous solution of ammonium hydroxide, previously prepared for 1:1 dilution with water of a commercial aqueous solution (28%-30%, Sigma-Aldrich®), continuing to stir with a shaft stirrer with a Teflon half-moon blade, monitoring the pH with a Metrohm glass electrode (Syntrode 518 mm with Pt 1000, catalogue no. 6.0248.030), connected to a Metrohm pHmeter mod. 780. After the addition, the measured pH was 10.2. The suspension obtained was filtered and the solid phase was washed with 2 L of water and subsequently dried in an oven at 120° C. for 2 hours. To obtain a sufficient quantity of active catalytic phase, various preparations conducted as described above were joined together.

1270 g of the material obtained, after sieving through a sieve with 0.125 mm mesh, was mixed dry for 1 hour in a planetary stirrer mounted on the motor of an Erweka oscillating granulator mod. AMD, then, in a first step lasting 50 minutes, 180 g of an aqueous solution at 25% by weight of ammonium hydroxide were added, previously prepared by dilution of the commercial aqueous solution (28%-30%, Sigma-Aldrich®), and in a second phase, over another 50 minutes, 160 ml of demineralized water.

The pasty mass obtained was transferred into a Bepex Hutt (Hosowaka-Bepex) extruder equipped with rollers with 2 mm holes, and extruded in pellets. After drying in the air for 48 hours, 100 g of pellets were subjected to calcination at a temperature programmed according to the following gradient: from room temperature to 800° C. with a ramp of 1° C./min; 800° C. constant for 6 hours.

After cooling, the pellets were mechanically granulated and the fraction of granules having dimensions comprised between 0.5 mm and 1 mm was used as catalytic material.

Process of Catalytic Dehydration of 1,3-Butanediol

The dehydration reaction of the 1,3-butanediol was performed in a AISI 316L steel fixed bed tubular reactor, having a length of 400 mm and internal diameter of 9.65 mm. Inside the reactor and along its axis, in a well having an external diameter of 3 mm, a thermocouple was placed for regulating the temperature.

The reactor was placed in an oven with electric heating that provided the heat necessary for the reaction.

3 g of the catalyst prepared as described above were placed in the reactor between two layers of inert material based on corundum. The catalytic bed was kept in place through a sintered steel baffle placed on the bottom of the reactor. The reactor was set with a down-flow arrangement.

The catalyst was pre-treated in situ at 300° C., under a flow of nitrogen (N$_2$). Then 30 g/h of a mixture of 1,3-butanediol (99%, Fluka) and water in the molar ratio [butanediol]/[water]=1.2 were added to the reactor.

The feeding was performed from the top of the reactor, at atmospheric pressure (0.1 MPa), at the first zone containing inert material having an evaporator function, so as to allow the reagents to reach the reaction temperature before coming into contact with the catalyst. The liquid reagents were then fed through an HPLC (High Performance Liquid Chromatography) pump, while the gases were fed through a Thermal Mass Flow-Meter (TMF). Downstream of the reactor, the products obtained were cooled in a heat exchanger and the condensed liquid was collected in hermetic glass bottles, while the gases were sent to a wet gas flow meter in order to measure its volume, while a small part of them was sent for gas-chromatography analysis, performed with an Agilent HP7890 gas-chromatograph with HP-Al/S column 50 m in length, 0.53 mm in diameter, 15 μm of film, helium at 30 cm/s as a carrier gas and flame ionization detector (FID). The quanti-qualitative analysis was performed using an external standard and making reference to calibration curves for the individual known components of the gaseous mixture.

The characterization of the liquid products was performed using gas-chromatography analysis using an Agilent HP 7890 gas-chromatograph equipped with a split/splitless injector, on a Quadrex® FFAP column 25 m in length, 0.32 mm in diameter, 1 μm film thickness, using helium at 50 cm/s as a carrier gas and flame ionization detector (FID). The quantitative analysis was performed using an internal standard and making reference to calibration curves for the individual known components.

The catalytic performance levels are expressed by calculating the conversion of 1,3 butanediol, or 1,3-BDO ($C_{1,3\text{-}BDO}$), and the selectivity $S_i$ to the individual i-th butenols using the following formulae:

$$C_{1,3\text{-}BDO} = \frac{(mol_{i_{1,3\text{-}BDO}})_{in} - (mol_{i_{1,3\text{-}BDO}})_{out}}{(mol_{i_{1,3\text{-}BDO}})_{in}} \times 100$$

$$S_i = \frac{mol_{i}}{(mol_{i_{1,3\text{-}BDO}})_{in} - (mol_{i_{1,3\text{-}BDO}})_{out}} \times 100$$

wherein
mol$_i$=moles of the i-th butenol produced;
(mol$_{i_{1\text{-}3\text{-}BDO}}$)$_{in}$=moles of 1,3-butanediol at the reactor inlet;
(mol$_{i_{1\text{-}3\text{-}BDO}}$)$_{out}$=moles 1,3-butanediol at the reactor outlet.

Table 1 below shows the results obtained in different experiments conducted at different temperatures and contact times between the catalyst and the feed current under the process conditions (Time on Stream).

TABLE 1 operating conditions and results of the dehydration of 1,3-butanediol with cerium oxide based catalyst

| Time on Stream (h) | Temperature (° C.) | $C_{1,3\text{-}BDO}$ (%) | $S_i$ (%) |
|---|---|---|---|
| 99 | 380 | 83 | 97 |
| 216 | 380 | 84 | 98 |
| 412 | 385 | 85 | 96 |
| 608 | 385 | 88 | 96 |
| 846 | 385 | 86 | 98 |
| 854 | 388 | 88 | 93 |

The mixture of butenols at the outlet of the reactor was purified by distillation and diluted with water obtaining an aqueous solution of isomer butenols having the composition of Table 2 below:

TABLE 2 composition of mixture of butenols

| Component | Percentage quantity |
|---|---|
| 2-buten-1-ol | 32.5% |
| 3-buten-2-ol | 35.5% |
| 3-buten-1-ol | 0.4% |
| water | 31.6% |

EXAMPLES 10-15

Catalytic Dehydration Tests on a Mixture of Butenols

The catalytic dehydration tests were conducted using the catalytic material prepared as described in Examples 1 to 5 reported above.

Furthermore, the activity of a commercial catalyst comprising zeolite Y having SAR=12, was determined, formed in the presence of alumina as a binder (Extrudate Zeolyst™ International CBV 712 CY 1.6, Example 15).

3 g of catalytic material (pellets having dimensions comprised between 0.5 and 1 mm) were loaded into an AISI 316L steel fixed bed tubular reactor, having a length of 350 mm and internal diameter of 9.65 mm, between two layers of inert material based on corundum. The catalytic bed was kept in place through a sintered steel baffle placed on the bottom of the reactor. The reactor was set with a down-flow arrangement.

Inside the reactor and along its axis, in a well having an external diameter of 3 mm, a thermocouple was placed for regulating the temperature.

The reactor was placed in an oven with electric heating that provided the heat necessary for the reaction.

The catalytic material was pre-treated in situ at 300° C., under a flow of nitrogen ($N_2$) for about 2 hours.

Then 7.3 g/h of mixture of butenols having the composition of Table 2 were fed to the aforementioned reactor, to which further water was added, as described below.

The feeding was performed from the top of the reactor, at atmospheric pressure (0.1 MPa), at the first zone containing inert material having an evaporator function, so as to allow the reagents to reach the reaction temperature before coming into contact with the catalyst. The load was fed through an ISCO D500 pump. Downstream of the reactor, the gaseous products obtained were diluted with a constant volume of gaseous nitrogen ($N_2$), cooled in a heat exchanger and the condensed liquid was collected in hermetic glass bottles, while the gases were sent to a wet gas flow meter in order to measure its volume, while a small part of them was sent for gas-chromatography analysis, performed with an Agilent HP6890 gas-chromatograph with HP-Al/S column 50 m in length, 0.53 mm in diameter, 15 μm of film, helium at 30 cm/s as a carrier gas and flame ionization detector (FID). The quantitative analysis was performed using an external standard and making reference to calibration curves for the individual known components of the gaseous mixture.

The characterization of the liquid products was performed using gas-chromatography analysis using an Agilent HP 7890 gas-chromatograph equipped with a split/splitless injector, on a Quadrex® FFAP column 25 m in length, 0.32 mm in diameter, 1 μm film thickness, using helium at 50 cm/s as a carrier gas and flame ionization detector (FID). The quantitative analysis was performed using an internal standard and making reference to calibration curves for the individual known components.

The catalytic performance levels were expressed by calculating the conversion of butenols ($C_{butenoli}$), and the selectivity to 1,3-butadiene (1,3-BDE) $S_{1,3\text{-}BDE}$, using the following formulae:

$$C_{butenoli} = \frac{(moli_{butenoli})_{in} - (moli_{butenoli})_{out}}{(moli_{butenoli})_{in}} \times 100$$

$$S_{1,3\text{-}BDE} = \frac{moli_{1,3\text{-}BDE}}{(moli_{butenoli})_{in} - (moli_{butenoli})_{out}} \times 100$$

in which:

$(moli_{butenoli})_{in}$=moles of butenols at the reactor inlet;

$(moli_{butenoli})_{out}$=moles of butenols at the reactor outlet;

$moli_{1,3\text{-}BDE}$=moles of 1,3-butadiene produced.

Table 3 below shows the catalyst used, the molar ratio SAR in the active phase of the catalyst, the temperature at which the catalytic dehydration and the weight hourly space velocity (WHSV), i.e. the ratio between the weight of the butenols fed in the unit of time and the weight of the catalyst, the contact time, calculated as a ratio between the volume of material loaded and the volumetric feed rate under the reaction conditions, the molar ratio [water]/[butenols] fed, which considers the water already present in the mixture of butenols and any more added, the time on stream, i.e. the time in which the catalyst remained in contact with the feed stream under the process conditions and during which the conversion of butenols fed is higher than 80%, the average selectivity to 1,3-butadiene, the average conversion of butenols, both referring to the time on stream of the test, the productivity expressed in terms of kg of 1,3-butadiene produced per kg of zeolitic catalyst.

TABLE 3

Results of catalytic tests

| Example | Zeolite | Binder | Example prep. | SAR | Temperature (° C.) | WHSV(h$^{-1}$) | τ (s) | [water]/ [butenols] | Time on Stream (h) | S1,3-BDE (%) | Productivity (kg$_{1,3BDE}$/kg$_{cataliz}$) | C$_{butenoli}$ (%) |
|---|---|---|---|---|---|---|---|---|---|---|---|---|
| 10 | Y | SiO$_2$ | 1 | 12 | 300 | 1.9 | 2 | 2 | 60 | 96 | 73 | 91 |
| 11 | Y | SiO$_2$ | 2 | 30 | 300 | 2.2 | 2.8 | 1.6 | 30 | 86 | 39 | 91 |
| 12 | Y | Al$_2$O$_3$ | 3 | 12 | 300 | 4.8 | 0.9 | 2.6 | 20 | 75 | 49 | 91 |
| 13 | Beta | Al$_2$O$_3$ | 4 | 28 | 315 | 1.8 | 1.6 | 2.3 | 75 | 93 | 86 | 94 |
| 14 | Beta | SiO$_2$ | 5 | 25 | 315 | 1.8 | 1.3 | 2.3 | 30 | 94 | 37 | 97 |
| 15 | Y | Al$_2$O$_3$ | — | 12 | 300 | 2.1 | 1.6 | 1.6 | 30 | 74 | 31 | 89 |

From the data in Table 3 it can be deduced that the use of catalytic materials comprising macroporous zeolites, and in particular a zeolite Y or a zeolite Beta in acid form having an SAR comprised between 7 and 60 and preferably comprised between 10 and 30, allows excellent conversions of butenols and excellent selectivity and productivity to 1,3-butadiene to be obtained.

In particular, it is observed that the best results are obtained when the catalytic material comprises a zeolite Y in acid form, formed in the presence of SiO$_2$ as a binder or a zeolite Beta in acid form, formed in the presence of Al$_2$O$_3$ as a binder.

COMPARATIVE EXAMPLES 16-19

Catalytic Dehydration Tests on a Mixture of Butenols

The catalytic materials, prepared as described in the Examples from 6 to 8 reported above, were subjected to the catalytic dehydration test of a mixture of butenols under the conditions of Examples 10-15 reported above.

Furthermore, in another catalytic test, the activity was determined of the y-alumina obtained by the calcination of pseudo-boehmite Versal™ V 250 UOP at about 600° C. (Example 19).

Table 4 below shows the results of the catalytic tests:

The γ-alumina, advantageously used in the dehydration of ethanol to ethylene, in the dehydration process of alkenols according to the present invention demonstrates instead poor selectivity and productivity.

EXAMPLE 20

Regeneration of the Catalyst

The catalytic material prepared as described in Example 1 and used in the catalytic test as described in Example 10 was regenerated by oxidative combustion of the carbon residues. The regeneration process requires a heat treatment of the catalytic bed at the temperature of 450° C. and the flushing of the catalytic material with molecular nitrogen (space velocity GHSV=15001 h$^{-1}$) for about 2 hours. At the end, the gas was gradually exchanged, from N$_2$ to air, over 1 hour, maintaining the space velocity constant (GHSV=1500 h$^{-1}$). By completing the exchange, a flow of air was maintained at 450° C. for 10 hours, to guarantee the combustion of the carbon residues present on the matrix of the catalytic material itself. Finally, the air was substituted again with N$_2$ and the temperature was brought to 300° C. to start a possible new reaction cycle.

TABLE 4 results of catalytic tests

| Example | Zeolite | Binder | Example prep. | SAR | Temperature (° C.) | WHSV(h$^{-1}$) | τ (s) | [water]/ [butenols] | Time on Stream (h) | S1,3-BDE (%) | Productivity (kg$_{1,3BDE}$/kg$_{cataliz}$) | C$_{butenoli}$ (%) |
|---|---|---|---|---|---|---|---|---|---|---|---|---|
| 16 | Y | SiO$_2$ | 6 | 5.2 | 300 | 2.1 | 1.5 | 1.6 | 15 | 78 | 17 | 89 |
| 17 | ZSM-5 | SiO$_2$ | 7 | 23 | 300 | 2.1 | 1.4 | 1.6 | 15 | 87 | 20 | 95 |
| 18 | ZSM-5 | SiO$_2$ | 8 | 80 | 300 | 2.1 | 1.2 | 1.6 | 1.5 | N.A. | N.A. | <<80 |
| 19 | γ-Al$_2$O$_3$ | — | — | — | 300 | 4 | 0.9 | 1.9 | 6 | 42 | 6 | 83 |

From the data presented in Table 4, it is clear that the use of a catalytic material comprising a zeolite Y in acid form having an SAR not comprised between 7 and 60 demonstrates overall less satisfactory activity with respect to those having the characteristics presented in Table 3. Without wishing to connect to any theory, the SAR hence appears to regulate the activity of the zeolites, influencing their selectivity for the substrate.

Likewise, catalytic materials comprising the mesoporous zeolite ZSM-5 demonstrate overall less satisfactory results with respect to the macroporous zeolites with the characteristics presented in Table 3.

EXAMPLE 21

Reaction and Regeneration Tests

The catalytic material prepared as described in Example 1 was subjected to 10 reaction and regeneration cycles through oxidative combustion of the carbon residue. The reaction was conducted as described in Example 10, with the consistent variation in dilution, over the first two reaction cycles, of the reaction mixture with N$_2$ in a ratio of 1.66:1 with the mixture of butenols.

At the end of each reaction cycle, lasting 36 hours, the aforementioned catalytic material was regenerated in situ as described in Example 21.

The results of the test were presented in the following Table 5, in which "But" indicates butenols while BDE indicates 1,3-butadiene.

TABLE 5

Reaction and regeneration tests using a catalyst based on zeolite Y (SAR = 12) formed in the presence of $SiO_2$ as a binder.

| Cycle | T [°C.] | WHSV [h$^{-1}$] | τ [s] | Dilution of the reaction mixture | | Productivity per reaction cycle [kg$_{BDE}$/kg$_{cat}$] | Conv. [%] | Select. [%] |
|---|---|---|---|---|---|---|---|---|
| | | | | H$_2$O/But | N$_2$/But | | | |
| 1 | 300 | 2.25 | 2.66 | 1.95 | 1.66 | 45.0 | 80.4 | 91.8 |
| 2 | 300 | 2.25 | 2.65 | 1.95 | 1.66 | 44.9 | 80.7 | 90.8 |
| 3 | 300 | 3.01 | 3.43 | 2.02 | 0.03 | 59.7 | 86.8 | 82.0 |
| 4 | 300 | 2.87 | 3.55 | 2.02 | 0.02 | 59.8 | 86.2 | 89.4 |
| 5 | 300 | 2.25 | 3.41 | 2.71 | 0.03 | 51.7 | 96.5 | 88.0 |
| 6 | 300 | 2.22 | 3.42 | 2.71 | 0.03 | 51.0 | 92.4 | 91.9 |
| 7 | 300 | 2.24 | 3.44 | 2.71 | 0.03 | 51.9 | 96.4 | 89.5 |
| 8 | 300 | 2.24 | 3.43 | 2.71 | 0.03 | 52.4 | 95.0 | 91.0 |
| 9 | 300 | 2.24 | 3.49 | 2.71 | 0.03 | 53.4 | 95.2 | 92.7 |
| 10 | 300 | 2.23 | 3.50 | 2.71 | 0.03 | 52.3 | 95.1 | 91.2 |

It is clear that the conversion yield and the selectivity of the catalyst comprising a macroporous zeolite may undergo a high number of regenerations without any reductions being noted in the conversion yield or selectivity.

Finally, it is however to be understood that further changes and variations may be made to the process described and illustrated herein which do not depart from the scope of the appended claims.

The invention claimed is:

1. A process for producing a conjugated diene comprising:
obtaining at least one alkenol selected from the group consisting of commercial alkenols, alkenols obtained from a biosynthetic process, and alkenols obtained by a catalytic dehydration, said at least one alkenol comprising a linear or branched alkenol having the general formula $C_nH_{2n}O$, wherein n is an integer greater than or equal to 4 and less than or equal to 8,
dehydrating said at least one alkenol in the presence of at least one catalytic material comprising at least one macroporous zeolite having an FAU, BEA, or MTW structure in acid form, or prevalently acid form, to produce a product comprising the conjugated diene,
wherein said at least one macroporous zeolite has a molar ratio of $SiO_2/Al_2O_3$ between 7 and 60,
wherein said at least one catalytic material comprises at least one inorganic binder selected from the group consisting of silica, alumina, zirconium oxide, titanium oxide and mixtures thereof, in a quantity of 5% to 80% by weight relative to a total weight of said at least one catalytic material,
provided that if said at least one alkenol is derived from catalytic dehydration of at least one diol, said catalytic dehydration of at least one diol is performed under different conditions as a previous dehydration step occurring prior to the dehydrating at least one alkenol.

2. The process according to claim 1, wherein said at least one zeolite having a FAU structure is a zeolite Y.

3. The process according to claim 2, wherein said zeolite Y is characterized by a molar ratio of $SiO_2/Al_2O_3$ of between 12 and 30.

4. The process according to claim 3, wherein said at least one catalytic material comprises an inorganic binder containing silica.

5. The process according to claim 1, wherein said at least one macroporous zeolite having a BEA structure is zeolite Beta.

6. The process according to claim 5, wherein said zeolite Beta is characterized by a molar ratio of $SiO_2/Al_2O_3$ of between 25 and 30.

7. The process according to claim 6, wherein said at least one catalytic material comprises an inorganic binder comprising alumina.

8. The process according to claim 1, wherein said at least one alkenol is selected from the group consisting of 2-buten-1-ol, 3-buten-2-ol, 3-buten-1-ol and mixtures thereof.

9. The process according to claim 1, wherein said at least one alkenol is selected from the group consisting of alkenols obtained directly from a biosynthetic process and alkenols obtained by a catalytic dehydration process of at least one diol.

10. The process according to claim 9, wherein the at least one alkenol is an alkenol obtained by the catalytic dehydration process of at least one diol, and said diol is derived from fermentation of sugars.

11. The process according to claim 1, wherein said at least one alkenol is in a mixture with a diluent selected from an inert gas and a compound having a boiling point between 25° C. and 150° C. under normal conditions and a melting point less than or equal to 20° C. under normal conditions.

12. The process according to claim 11, wherein said compound is selected from the group consisting of water, tetrahydrofuran, cyclohexane, benzene, and mixtures thereof.

13. The process according to claim 11, wherein said diluent is selected from the group consisting of $N_2$ and water.

14. The process according to claim 1, wherein the step of dehydrating said at least one alkenol is conducted at a temperature between 150° C. and 500° C.

15. The process according to claim 1, wherein the step of dehydrating said at least one alkenol is conducted at a pressure between 5 and 5000 kPa.

16. The process according to claim 1, wherein the step of dehydrating said at least one alkenol is conducted in a gas phase or a mixed liquid/gas phase.

17. A process for producing a conjugated diene comprising:
dehydrating at least one alkenol having a number of carbon atoms greater than or equal to 4 in the presence of at least one catalytic material comprising at least one macroporous zeolite in acid form, or prevalently acid form, to produce a product comprising the conjugated diene, wherein said at least one macroporous zeolite has a molar ratio of $SiO_2/Al_2O_3$ of between 7 and 60, wherein said at least one catalytic material comprises at least one inorganic binder selected from the group consisting of silica, alumina, zirconium oxide, titanium oxide and mixtures thereof, in a quantity of 5% to 80% by weight relative to a total weight of said at least one catalytic material, wherein the at least one alkenol is obtained by catalytic dehydration of at least one diol, and wherein the catalytic dehydration of said at least one diol is performed in a different reactor than the dehydrating of the at least one alkenol.

18. A process for producing a conjugated diene comprising:

dehydrating at least one alkenol having a number of carbon atoms greater than or equal to 4 in the presence of at least one catalytic material comprising at least one macroporous zeolite in acid form, or prevalently acid form, to produce a product comprising the conjugated diene, wherein said at least one macroporous zeolite has a molar ratio of $SiO_2/Al_2O_3$ of between 7 and 60, wherein the at least one alkenol is obtained by catalytic dehydration of at least one diol, and wherein said catalytic dehydration of at least one diol is performed under different conditions and prior to the dehydrating at least one alkenol.

\* \* \* \* \*